(12) United States Patent
Bikram-Liles et al.

(10) Patent No.: US 11,826,333 B2
(45) Date of Patent: Nov. 28, 2023

(54) BACTERICIDAL DEBRIDEMENT COMPOSITIONS FOR SURGICAL SITE INFECTIONS AND CHRONIC WOUND HEALING

(71) Applicant: DePuy Synthes Products, Inc., Raynham, MA (US)

(72) Inventors: Malavosklish Bikram-Liles, Paoli, PA (US); Charles Florek, Downingtown, PA (US); David A. Armbruster, West Chester, PA (US); Shireen Shaikh, Bear, DE (US); Kyra Woloszczuk, Churchville, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 79 days.

(21) Appl. No.: 17/193,196

(22) Filed: Mar. 5, 2021

(65) Prior Publication Data
US 2021/0275483 A1   Sep. 9, 2021

Related U.S. Application Data

(60) Provisional application No. 62/986,997, filed on Mar. 9, 2020.

(51) Int. Cl.
*A61K 31/201* (2006.01)
*A61P 31/04* (2006.01)
(Continued)

(52) U.S. Cl.
CPC .......... *A61K 31/201* (2013.01); *A61K 31/546* (2013.01); *A61K 31/7036* (2013.01);
(Continued)

(58) Field of Classification Search
CPC .... A61B 2017/00004; A61B 2017/561; A61B 2017/00893; A61B 17/72; A61B 17/70; A61B 17/8028; A61L 31/16; A61L 27/54; A61L 2430/02; A61M 31/002; A61K 8/361; A61K 45/06; A61K 8/4973; A61K 31/7036; A61K 2300/00; A61K 31/201;
(Continued)

(56) References Cited

U.S. PATENT DOCUMENTS 5,348,991 A   9/1994   Yoshikawa et al.
5,428,101 A   6/1995   Urano et al.
(Continued)

OTHER PUBLICATIONS

Marques et al. Pharmaceuticals, 2015, 8, 816-835 (Year: 2015).*
(Continued)

*Primary Examiner* — Savitha M Rao
(74) *Attorney, Agent, or Firm* — BakerHostetler (57) ABSTRACT

Provided herein are compositions for treating biofilm-derived infections include a cis-monounsaturated fatty acid solubilized in a solvent with a concentration in the range of about 100 ppm (parts per million) to about 1000 ppm, where the composition is configured to produce a bactericidal effect measured as a log reduction of colony forming units (CFU) of a bacteria of at least 1.0 when the composition is applied to a biofilm formed from the bacteria. Also provided are methods for treating the site of a biofilm-derived infection comprising applying a composition as disclosed herein to the site.

31 Claims, 6 Drawing Sheets

(51) Int. Cl.
  *A61K 31/546* (2006.01)
  *A61K 31/7036* (2006.01)
  *A61K 38/14* (2006.01)
  *A61L 27/54* (2006.01)

(52) U.S. Cl.
  CPC .............. *A61K 38/14* (2013.01); *A61L 27/54* (2013.01); *A61P 31/04* (2018.01)

(58) Field of Classification Search
  CPC .. A61K 31/47; A61K 31/4709; A61K 31/496; A61K 31/4965; A61K 31/498; A61K 31/5383; A61K 31/546; A61K 31/606; A61K 31/7048; A61K 38/44; A61K 47/12; A61K 47/36; A61K 8/735; A61K 9/0056; A61K 9/0058; A61K 9/006; A61K 9/0075; A61K 9/1617; A61K 9/1623; A61P 1/02; A61P 1/04; A61P 13/02; A61P 13/08; A61P 15/02; A61P 17/00; A61P 17/02; A61P 17/10; A61P 27/16; A61P 29/00; A61P 31/00; A61P 31/04; A61P 11/00; C08L 75/04; A01N 37/18; A01N 37/02; A01N 37/06
  See application file for complete search history.

(56) References Cited

U.S. PATENT DOCUMENTS

| | | | |
|---|---|---|---|
| 5,556,913 | A | 9/1996 | Tobinaga et al. |
| 8,513,305 | B2 | 8/2013 | Davies |
| 8,993,540 | B2 | 3/2015 | Haggard et al. |
| 9,359,472 | B2 | 6/2016 | Nicholson et al. |
| 9,642,948 | B2 | 5/2017 | Haggard et al. |
| 9,662,400 | B2 | 5/2017 | Smith et al. |
| 9,801,909 | B2 | 10/2017 | Wood et al. |
| 2019/0365868 | A1* | 12/2019 | Sauer .................. A61K 31/7036 |

OTHER PUBLICATIONS

Davies, D. G. & Marques, C.N. (2009). A fatty acid messenger is responsible for inducing dispersion in microbial biofilms. J Bacteriol., 191, 1393-1403.

Demidova-Rice, T. A. et al. (2012). Acute and Impaired Wound Healing: Pathophysiology and Current Methods for Drug Delivery, Part 1: Normal and Chronic Wounds: Biology, Causes, and Approaches to Care. Adv Skin Wound Care, 25(7), 304-314.

Desbois, A.P. and Smith, V.J (2010). Antibacterial free fatty acids: activities, mechanisms of action and biotechnological potential. Applied Microbiol. Biotechnol., 85(6), 1629-42.

Dow, JM et al. (Sep. 2003). Biofilm dispersal in Xanthomonas campestris is controlled by cell-cell signaling and is required for full virulence to plants. Proc. Natl. Acad. Sci., 100(19), 10995-1000.

Jennings J.A. et al. (2012). Cis-2-decenoic Acid Inhibits *S. aureus* Growth and Biofilm In Vitro: A Pilot Study. Clin Orthop Relat Res., 470, 2663-2670.

Mirani Z.A. et al. (2017). Antibacterial fatty acids destabilize hydrophobic and multicellular aggregates of biofilm in *S. aureus*, The Journal of Antibiotics, 115-121.

Olsen I. (2015). Biofilm-specific antibiotic tolerance and resistance. Eur. J. Clin. Microbiol. Infect. Dis., 34(5), 877-886.

Payne, W.G. et al. (2008). Enzymatic Debriding Agents Are Safe in Wounds With High Bacterial Bioburdens and Stimulate Healing. EPlasty—Journal of Plastic Surgery, 8(e7), 151-156.

Pourmoussa, A. et al. (2016). An update and review of cell-based wound dressings and their integration into clinical practice. Annals of Translational Medicine, 4(23), 457-66.

Rabin, N. et al. (2015). Agents that inhibit bacterial biofilm formation. Future Medicinal Chemistry, 7(5), 647-71.

Stenz, L. et al. (2008). Impact of oleic acid (cis-9-octadecenoic acid) on bacterial viability and biofilm production in *Staphylococcus aureus*. FEMS Microbial. Lett., 287(2), 149-155.

Worthington, R.J. et al. (2012). Small molecule control of bacterial biofilms, Org Biomol Chem., 10(37), 7457-7474.

* cited by examiner

BACTERICIDAL DEBRIDEMENT COMPOSITIONS FOR SURGICAL SITE INFECTIONS AND CHRONIC WOUND HEALING

CROSS-REFERENCE TO RELATED APPLICATIONS

This application claims the benefit of priority to U.S. Provisional Application No. 62/986,997, filed Mar. 9, 2020, the entire contents of which are incorporated herein by reference.

FIELD OF DISCLOSURE

The present disclosure is directed to compositions having bactericidal effects on bacterial biofilms. The compositions include cis monounsaturated fatty acids, such as cis-2-alkenoic acids in concentrations in the range of about 100 ppm to 1000 ppm. The compositions can further include one or more antibiotic drugs. The present disclosure additionally describes method of treatment using these compositions.

BACKGROUND

Infections stemming from bacterial biofilm formation in the body are the cause of substantial medical costs and morbidity.

One of the main bacterial causes in orthopedic implant related infections is *Staphylococcus aureus*, which form biofilms both on the implanted device as well as the surrounding tissues. Established biofilms on medical devices can have deleterious effects including surgical intervention and secondary complications. Biofilm related infections are typically resistant to systemic levels of antimicrobials.

Chronic wounds are wounds that do not re-epithelialize after 3 months (see Pourmoussa, A. et al. (2016). An update and review of cell-based wound dressings and their integration into clinical practice. Annals of Translational Medicine, 4(23), 457-66). In the United States, over 4 million patients suffer with chronic wounds at a cost in excess of $50 billion. The pathophysiology of chronic wounds includes persistent infections, uncontrolled inflammation, drug-resistant microbial biofilms, and a loss of dermal and/or epidermal cells' ability to respond to reparative stimuli.

In both cases, the bacterial infections result in the attachment of bacteria to the device or surface of the wound, which eventually leads to the formation of biofilm. Biofilms are intrinsically resistant to antibiotics and it has been reported that for bacteria in the biofilm phenotype, 10 to 1000 times higher therapeutic concentrations are required to eradicate the pathogens vs. their planktonic counterparts, which is clinically unattainable because such dosage levels vastly exceed the maximum effective concentration (MEC) of those drugs (see Olsen I. (2015). Biofilm-specific antibiotic tolerance and resistance. Eur. J. Clin. Microbiol. Infect. Dis., 34(5), 877-886). Therefore, surgical intervention is typically required in addition to antibiotics to treat the infected site. The cells within a biofilm are embedded within a hydrated protective extracellular polymeric substance (EPS). One approach to treating bacterial infections is to try and dismantle the EPS/biofilm and disperse the indwellers to their planktonic state, restoring their susceptibility to systemic treatment levels of antimicrobial agents in an acceptable range below the MEC.

Attempts have been made to disrupt the biofilm through debridement and dispersants. Debridement is one way to promote wound healing and management. Debridement is the removal of debris (nonviable materials, foreign bodies, visible biofilm, and poorly healing tissue) from a wound that thereby facilitates the processes of granulation, contraction, epithelialization, and healing (see Payne, W. G. et al. (2008). Enzymatic Debriding Agents Are Safe in Wounds With High Bacterial Bioburdens and Stimulate Healing. EPlasty—Journal of Plastic Surgery, 8(e7), 151-156). Therefore, the process of debridement can contribute to the disruption of biofilm from a site of infection to increase tissue healing.

The most common form of debridement is surgical excision, which can be limited by poor patient candidates. Alternative debridement options can include mechanical debridement such as wet to dry dressings or pressure irrigation; autolytic debridement, where occlusive dressings allow wound proteases to liquefy necrotic tissue; biologic debridement such as maggot therapy; and enzymatic debridement that utilizes agents such as collagenase or papain-urea.

Another approach that can be used, either alone or in conjunction with debridement, is the use of bacterial dispersants that can biochemically disrupt the biofilm to release bacteria from their protective environment and aid in the restoration of antimicrobial susceptibility. One class of compounds that can provide bacterial dispersion is cis monounsaturated fatty acids, such as cis-2-alkenoic acids. Fatty acids belonging to this class of cis monounsaturated fatty acids that have been shown to be effective biofilm disruptors includes cis-2-decenoic acid, cis-9-octadecanoic acid (oleic acid), and cis-11-methyl-2-dodecenoic acid (see Rabin, N. et al. (2015). Agents that inhibit bacterial biofilm formation. Future Medicinal Chemistry, 7(5), 647-71; Worthington, R. J. et al. (2012). Small molecule control of bacterial biofilms, Org Biomol Chem., 10(37), 7457-7474). Oleic acid has been shown to repress biofilm formation of *Staphylococcus aureus* by inhibiting bacterial adhesion (see Stenz, L. et al. (2005). Impact of oleic acid (cis-9-octadecenoic acid) on bacterial viability and biofilm production in *Staphylococcus aureus*. FEMS Microbial. Lett., 287(2), 149-155). Cis-2-decenoic acid is produced from *P. aeruginosa* and has been shown to disperse established biofilms across many species of bacteria and across kingdom including *P. aeruginosa, E. coli, K pneumoniae, Proteus mirabilis, Streptococcus pyogenes, B. subtilis, S. aureus*, and the yeast *C. albicans* (see Rabin, N. et al. (2015)—cited in full above). And cis-11-methyl-2-dodecenoic acid has been shown to disaggregate cell flocs by *Xanthomonas campestris* (see Dow, J M et al. (2003). Biofilm dispersal in *Xanthomonas campestris* is controlled by cell-cell signaling and is required for full virulence to plants. Proc. Natl. Acad. Sci., 100(19), 10995-1000). In addition, studies have shown that cis-2-decenoic acid was able to disperse biofilms with concentrations as low as about 2.5 nM (see Davies, D. G. & Marques, C. N. (2009). A fatty acid messenger is responsible for inducing dispersion in microbial biofilms. J Bacteriol., 191, 1393-1403).

However, despite these options, wound care management remains a challenge due to pathophysiological issues and hence the development of new and effective treatments of biofilm infections remains a healthcare need.

SUMMARY

The compositions described in the present disclosure are unique as they are intended to target biofilm-associated bacteria instead of planktonic bacteria. Biofilm-derived infections remain a major challenge for wound debridement and healing. Currently, there are limited debridement aids that are able to effectively target biofilm-associated and multidrug resistant bacteria and as such the compositions of the present disclosure can represent an improvement over the present standard of care.

The present disclosure is therefore directed to new bactericidal compositions for the use in inhibiting and treating biofilm-derived infections. According to embodiments of the present disclosure, compositions for treating biofilm-derived infections include a cis-monounsaturated fatty acid solubilized in a solvent with a concentration in the range of about 100 ppm (parts per million) to about 1000 ppm, where the composition is configured to produce a bactericidal effect measured as a log reduction of colony forming units (CFU) of a bacteria of at least 1.0 when the composition is applied to a biofilm formed from the bacteria. In certain embodiments, the compositions described herein can additionally include one or more antibiotic drugs.

According to further embodiments of the present disclosure, a method of treating a biofilm-derived infection site is described including the steps of identifying a site including a biofilm and applying a bactericidal composition of the present disclosure to the site.

According to additional embodiments of the present disclosure, a method of inhibiting biofilm formation at a wound or surgical site is described including the steps of identifying a wound or surgical site susceptible to biofilm-derived infection and applying a bactericidal composition of the present disclosure.

DETAILED DESCRIPTION

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range. It is also to be appreciated that certain features of the invention, which, for clarity, are described herein in the context of separate embodiments, may also be provided in combination in a single embodiment. Conversely, various features of the invention that are, for brevity, described in the context of a single embodiment, may also be provided separately or in any subcombination.

As used herein "log reduction" or derivations thereof, means the log value difference in the number of colony forming units (CFUs) between an untreated biofilm, and one with a test composition applied to the biofilm. In other words, log reduction=log CFU (biofilm)−log CFU (treated biofilm).

According to embodiments of the present disclosure, compositions for treating biofilm-derived infections include a cis-monounsaturated fatty acid solubilized in a solvent with a concentration in the range of about 100 ppm to about 1000 ppm, where the composition is configured to produce a bactericidal effect measured as a log reduction of colony forming units (CFU) of a bacteria of at least 1.0 when the composition is applied to a biofilm formed from the bacteria. It is contemplated that the compositions described herein are effective against both gram-positive bacteria and gram-negative bacteria, as well as certain fungus, in particular yeasts such as C. albicans.

According to preferred embodiments of the present disclosure the cis-monounsaturated fatty acid is a cis-2-alkenoic acid. According to still further preferred embodiments, the cis-2-alkenoic acid is cis-2-decenoic acid (CDA), cis-9-octadecanoic acid (oleic acid), or cis-11-methyl-2-dodecenoic acid, or any combination thereof. In a most preferred embodiment, the cis-2-alkenoic acid is CDA, or a combination including CDA.

According to embodiments of present disclosure, the cis-monounsaturated fatty acid is solubilized in a solvent. Suitable solvents for dissolving cis-monounsaturated fatty acids are known and can be readily determined by one of skill in the art. Preferred solvents are those which the U.S. Food and Drug Administration have approved as safe for use in humans. Exemplary solvents can include dimethyl sulfoxide (DMSO) and ethanol.

According to embodiments of the present disclosure, the concentration of the cis-monounsaturated fatty acid in the composition is in the range of about 100 ppm to about 1000 ppm. The use of ppm is meant to indicate the concentration of the solute in the composition. For example, the concentration can be in the range of about 100 ppm to about 800 ppm, about 200 ppm to about 800 ppm, about 200 ppm to about 500 ppm, about 200 ppm to about 400 ppm, about 400 ppm to about 500 ppm, about 400 ppm to about 800 ppm, about 400 ppm to about 1000 ppm, about 500 ppm to about 1000 ppm, and about 500 ppm to about 800 ppm, and include specific concentrations of any one of the beginning or ending points of the above listed ranges.

According to embodiments of the present disclosure, the compositions can additionally include one or more antibiotic drugs. The antibiotic drug can be present in a concentration range of about 1 ppm to about 15 ppm, for example in the range of about 1 ppm to about 10 ppm, from about 1 ppm to about 5 ppm, from about 5 ppm to about 10 ppm, or from about 10 ppm to 15 ppm, including specific concentrations of any one of the beginning or ending points of the above-listed ranges.

According to certain embodiments, the antibiotic drug is from the class of aminoglycosides, cephalosporins, or glycopeptide antibiotics, or combinations of the same, such as, for example gentamicin, cefazolin, vancomycin, or combinations thereof.

According to certain embodiments of the present disclosure, the composition, when it includes an antibiotic drug, has a log reduction in the range of 2.0 to 6.5 greater than a corresponding log reduction of a composition comprising the antibiotic drug in the absence of the cis-monounsaturated fatty acid.

According to certain embodiments, an infection site being treated includes a mature biofilm that has grown for at least 48 hours. Without being bound by any particular theory, it is believed that the robustness of the biofilm, i.e., its resistance to traditional systemic antibiotic treatments, is directly proportional to the maturity of the biofilm. In certain embodiments, the biofilm is attached to the surface of live tissue (e.g., bone, muscle, skin, facia, etc.). In certain additional embodiments, one or more implantable medical devices are located at the infection site, and the biofilm is attached to an outer surface of the implantable medical device.

According to embodiments of the present disclosure, the composition produces a log reduction in the range of at least about 4.0 to about 8.0, for example in the range of about 4.0 to 6.0, from about 6.0 to about 8.0, from about 4.0 to about 5.0, from 5.0 to about 8.0, from about 5.0 to about 6.0, including specific log reduction vales of any one of the beginning or ending points of the above-listed ranges. In certain embodiments, the log reduction value is at least 4.5.

According to certain embodiments, the log reduction value is after the biofilm has been exposed to compositions of the present disclosure for at least 12 hours. In certain further embodiments, the log reduction value is after the biofilm has been exposed to compositions of the present disclosure for at least 24 hours. In certain embodiments, the log reduction value is after the biofilm has been exposed to compositions of the present disclosure for at least 1 hour.

Proposed Mechanism of Action

The bactericidal effects of the disclosed compositions on biofilms is an unexpected result based upon the present literature. Without being bound by any particular theory, and as will be shown in the examples below, the present inventors propose the following mechanisms of action whereby the fatty acid has demonstrated a bactericidal effect, both alone, and as an adjuvant in combination with an antibiotic.

In the planktonic or wild-type phenotypes, Mirani et al. have shown that methicillin resistant *Staphylococcus aureus* (MRSA) expresses an extracellular enzyme named fatty acid-modifying enzyme (FAME) (see Mirani Z. A. et al. (2016). Antibacterial fatty acids destabilize hydrophobic and multicellular aggregates of biofilm in *S. aureus*. The Journal of Antibiotics, 1-7). FAMEs inactivate the bactericidal activity of these fatty acids by their esterification to cholesterol at 6-12 hours of incubation. However, in robust mature biofilms of at least 48 hours, FAMEs are not detected likely due to the fact that previously planktonic bacteria are in their dormant state within a biofilm are unable to inactivate FAMEs. Thus, as a result they become more susceptible to the antibacterial effects of fatty acids of the type described herein.

In addition, fatty acids are known to have detergent-like properties due to their amphipathic structure (see Desbois, A. P. and Smith, V. J (2010). Antibacterial free fatty acids: activities, mechanisms of action and biotechnological potential. Applied Microbiol. Biotechnol., 85(6), 1629-42). This biochemical structure enables the fatty acid to interact with cellular membranes to create variable-sized pores that could be transient or permanent, which could enhance traditional antibiotic efficacy against the biofilm. Additionally, at high concentrations, these fatty acids can solubilize membranes that could result in lysis. Further contemplated mechanism of action that could contribute to cell inhibition or death of the bacteria in the biofilm include generation of toxic peroxidation and auto-oxidation products, inhibition of enzyme activity, and impairment of nutrient uptake.

Figure 1:
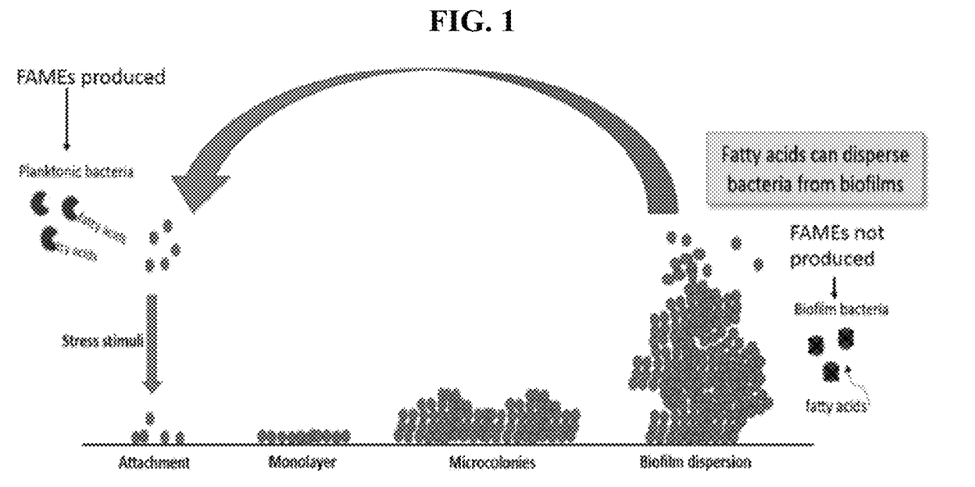
FIG. 1 provides a schematic representation of the effects of fatty acid dispersants on planktonic and biofilm bacteria.

Thus, in the planktonic state, FAMEs are produced by bacteria that are able to convert fatty acids such as CDA into inactive molecules of cholesterol that are not harmful to the bacteria. This is schematically represented in FIG. 1. Additionally, studies have shown the relatively high minimum inhibitory concentration (MIC) data for fatty acid effects on the planktonic bacteria. However, in the biofilm state, the bacteria do not produce FAMEs and cannot protect themselves from the fatty acid. The present inventors have discovered that in the presence of biofilm-associated bacteria, the fatty acids become bactericidal in certain advantageous concentration ranges. In the presence of antibiotics, the effects can be amplified, for example, in situations where pores are created by the fatty acid in the cell walls of the bacteria that enable antibiotics to access and thereby allow the fatty acid to act as an adjuvant.

In certain embodiments of the present disclosure, the composition can be applied as a solution, or can be applied where the composition is encapsulated in a liposome or micelle.

According to further embodiments of the present disclosure, a method of treatment is disclosed for treating a biofilm derived infection at an infection site including identifying a site including a biofilm, and applying the composition as described in the present disclosure to the site. The described method can include applying the composition one time to the infection site. Alternatively, the method can include multiple applications of the compositions to the infection site.

According to certain embodiments, the method can also include debriding at least a portion of the biofilm. Debridement techniques are known in the art, and examples of such techniques have been described above.

In certain embodiments, the infection site is the site of a chronic wound infection, or a surgical site. Exemplary surgical sites can include for example, a site where a mass such as a cyst or a tumor has been excised or otherwise removed, or can be a site where an implantable medical device has been inserted, as well as including any general surgical incision sites where the skin has been opened exposing tissue to the environment and therefore exposure to potential pathogens.

In embodiments including an implantable medical device at the infection site, the method can further include applying the composition to an outer surface of the medical device, as well as including applying the composition to tissue surrounding the medical device.

In embodiments of the present disclosure, the step of applying the composition can include first applying the composition to an absorbent material, such as, for example, gauze, wound dressings, sponges, or the like, and then subsequently applying or otherwise contacting the absorbent material to the infection site. Alternatively, the absorbent material can first be placed at the infection site and then subsequently the composition can be applied to the absorbent material, for example by common irrigation techniques. The use of absorbent materials can provide certain advantages by providing a reservoir of the composition at the infection site and prevent the rapid migration of the composition away from the infection site that could occur, for example, from irrigation techniques, or from increased blood flow to the infection site.

According to embodiments described in the present disclosure, another additional method of treatment can include utilizing the composition in preventative steps, such as, for example, in cases where a particular wound or surgical site is at a risk for becoming infected from a biofilm-derived infection. Such methods are directed to inhibiting, as opposed to treating, biofilm formation at a wound or surgical site. These methods can include identifying a wound or surgical site susceptible to biofilm-derived infection and applying embodiments of the composition as described in the present disclosure.

According to certain embodiments involving a surgical site, the surgical site is designed to receive an implantable medical device, and the method further includes the step of implanting the medical device to the surgical site. In certain embodiments, the composition can be applied to the site prior to the implantation of the device, or alternatively, after the device has been implanted. The method can further include applying the composition to an outer surface of the medical device. In certain embodiments, the composition is applied to the outer surface of the medical device before the medical device is implanted to the surgical site, and in alternative embodiments, the composition is applied to the outer surface of the medical device after the device is implanted to the surgical site.

EXAMPLES

Exemplary Clinical Debridement Procedure with Orthopedic Implants

Bactericidal compositions of the present disclosure can be used in combination with a surgical debridement process. Upon identification of an infection following orthopedic implantation, the surgeon can perform surgical or sharp debridement to excise necrotic tissue in an indiscriminate manner that removes both dead and viable tissue as is known in the art (see Demidova-Rice, T. A. ET AL. (2012). Acute and Impaired Wound Healing: Pathophysiology and Current Methods for Drug Delivery, Part 1: Normal and Chronic Wounds: Biology, Causes, and Approaches to Care. Adv Skin Wound Care, 25(7), 304-314). Compositions of the present disclosure can be utilized as a debridement aid to wash the surgical area and enhance targeted debridement of biofilm in and around the tissue. For example, CDA can be used to specifically target biofilm-associated bacteria as well as multidrug resistant bacteria with limited toxicity to healthy tissues.

Exemplary Fatty Acid

In the following examples, unless otherwise noted, cis-2-decenoic acid (CDA) was used for testing as a representative compound from the previously described class of cis-2-alkanoic acids that have been shown as possible bacterial dispersants. CDA was tested alone as a dispersant or debridement aid and was also tested in combination with antimicrobial drugs. The tests were conducted on representative medical devices inoculated with mature biofilms. The purpose of the below tests was to measure the effect of CDA alone as well as an adjuvant with common front-line antibiotics.

Mature Biofilm Growth

In the following examples, unless otherwise noted, testing was conducted on mature biofilms of S. aureus (ATCC 25923) that were grown for 48 hours. An exemplary preparation of the biofilm is as follows:

Prepare an overnight bacterial inoculum of S. aureus at a concentration of $10^9$ CFU/mL in 20 mL in commercial Tryptic Soy Broth (TSB) by incubating at 37° C. shaker at 250 rpm;

Take an OD600 reading of a diluted stock of overnight culture to determine stock concentration with the absorbance method;

Adjust the concentration of bacteria to $10^5$ CFU/mL using 0.3% (w/v) TSB forcibly aspirating up and down to break up clumps of colonies with a serological pipette from the stock concentration;

Plate the following dilutions in triplicates on TSA-L plates to determine the initial stock concentration of cells: $10^2$ CFU/mL;

Add 7 mL of inoculum into each 15 ml tube containing K-wire using a serological pipette, making sure to again forcibly aspirate up and down prior to addition;

Place the tubes on the revolver at 30° C.;

After 8 hours, unscrew the caps and transfer the caps with sutures to a new tube with 7 mL of 0.3% TSB and incubate in the shaker-incubator for an additional 44 hours to grow the biofilm at 40 RPM growing;

During this time, change the media 2 times per day by unscrewing the cap and transferring to a new tube with 7 mL TSB.

K-Wire Preparation

In the following examples, unless otherwise noted, 316L stainless steel K-Wires served as the exemplary implantable medical device.

New K-wires were roughened with #600 sandpaper (~10× along the length) followed by rinsing with deionized water. The rinsed K-wires were then completely immersed in a 10% citric acid (w/v) bath at ~49° C. for 20 minutes to passivate the surface of the stainless steel to prevent subsequent corrosion. After removal from the bath, the K-wires were then rinsed with deionized water. The K-wires were then washed and sterilized by autoclaving.

Preparation of Biofilm Formation on K-Wire and Subsequent CFU Count Methodology

K-wires were secured to tube caps and placed in tubes incubated with an initial inoculum concentration ($10^5$ CFU/mL) and grown for 24-48 hours. Media was changed roughly every 8 hours. After growth, the inoculated K-wires were ready for testing.

After exposure time is completed, both the well samples and the debrided K-wires are treated, and remaining bacteria cells are plated and counted. For the media in the wells, samples are centrifuged for 10 minutes at 3000 rpm and the supernatant is removed. The cells are resuspended in 10 mL 1×PBS buffer. This washing step is repeated for a 2nd time and the cells resuspended again in a final volume of 1.5 mL neutralizing buffer, diluted and plated on Tryptic Soy Agar with Lectin (TSA-L) agar plates. For the K-wires, the caps securing the K-wires in the tubes are removed and transferred to tubes with 10 mL 1×PBS and the tubes are inverted. The caps with the K-wires are transferred again to another tube with PBS and the step repeated. After washing the K-wires 2 times, they are transferred to tubes with neutralizing buffer and vortexed followed by ultra-sonication for 10 minutes. The cells are then diluted and plated on TSA-L agar plates.

Exemplary Mature Biofilm on K-Wire

Figure 2A:
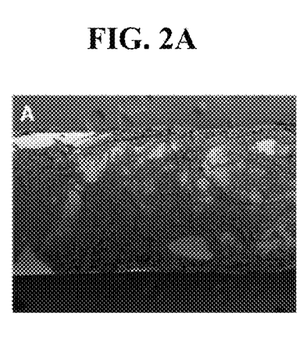
FIG. 2A-2C provide SEM images of a 48 hr biofilm grown on 316L stainless steel K-wires under 50× (FIG. 2A), 500× (FIG. 2B), and 5000× (FIG. 2C) magnification.
Figure 2B:
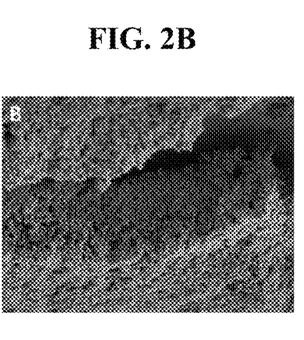
Figure 2C:
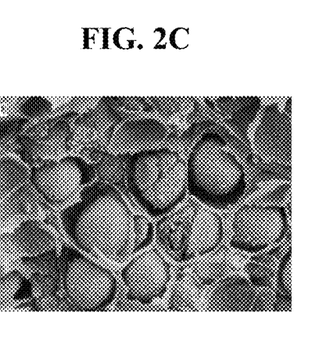

FIGS. 2A-2C depict the characterized morphology under scanning electron microscopy (SEM) for a mature biofilm growth on a K-wire according to the procedures outlined above.

Systemic Gentamicin Testing on Mature Biofilms

As a preliminary test, mature biofilms grown according to the procedures outlined above were subject to dosages of approximately 10 ppm (10 mcg/ml) gentamicin, which is approximately 10 times the generally recognized and accepted maximum systemic concentration of 1 mcg/ml. [Data not shown]. The tests showed that the mature biofilms were resistant to the gentamicin doses.

CDA Effect on Planktonic Bacteria

Figure 3A:
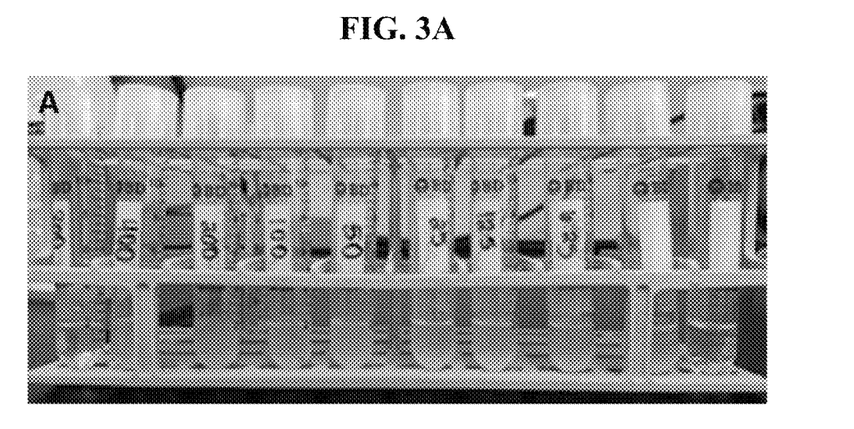
FIG. 3A shows the results of a test of the effect of different concentrations of CDA on planktonic bacteria, in which several different CDA concentrations (800 ppm, 400 ppm, 200 ppm, 100 ppm, 50 ppm, 25 ppm, 12.5 ppm, and 6.25 ppm) were placed in vials including planktonic S. aureus.

As an additional test, several different CDA concentrations (800 ppm, 400 ppm, 200 ppm, 100 ppm, 50 ppm, 25 ppm, 12.5 ppm, and 6.25 ppm) were placed in vials including planktonic *S. aureus*. The vials can be seen in FIG. 3A. Two controls are on the right and unlabeled (bacteria/no fatty acid and no fatty acid/no bacteria, respectively). The literature reports that CDA at concentrations ≥500 ppm inhibited the growth of MRSA and 125 ppm inhibited biofilm formation (see Jennings J. A. et al. (2012). Cis-2-decenoic Acid Inhibits *S. aureus* Growth and Biofilm In Vitro: A Pilot Study. Clin Orthop Relat Res., 470, 2663-2670). This test was qualitative and was based on whether there was observable bacteria in the test vials. In FIG. 3A, it can be seen that only the test vial containing 800 ppm CDA contains clear fluid, while the other tubes are all cloudy indicating active presence of bacteria. This test result indicated the minimum inhibitory concentration (MIC) of CDA to be 800 ppm for planktonic cells, significantly higher than suggested in the literature.

Figure 3B:
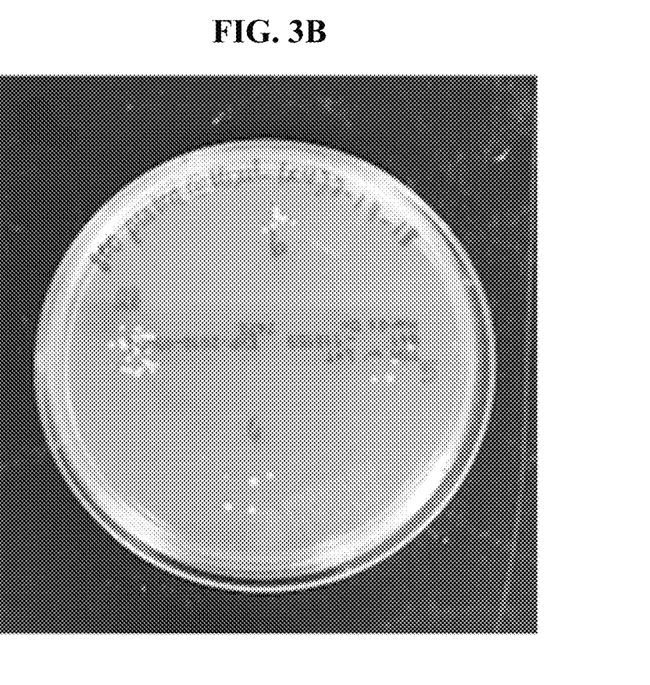
FIG. 3B depicts the results of a procedure in which 10 μL of the tube labelled '800' (see FIG. 3A) was plated onto a TSA-L agar plate that showed the growth of colonies after incubation of the tube at 24 hours.

Further even at that elevated concentration, CDA was found to be bacteriostatic, not bactericidal. This was confirmed in a follow up procedure where 10 μL of the tube labelled '800' (FIG. 3A) was plated onto a TSA-L agar plate that showed the growth of colonies after incubation of the tube at 24 hours as shown in FIG. 3B.

Thus, even at an MIC of 800 ppm, CDA was not shown to be bactericidal but rather bacteriostatic with respect to planktonic bacteria. In addition, the CDA sample at 400 ppm of CDA was shown to have visible growth in the tube that indicates no or limited toxicity to *S. aureus*.

CDA Dispersant Effect on Mature Biofilms

As previously noted, the literature suggests that concentrations of CDA as low as 2.5 nM were effective in dispersing biofilms. However, when mature biofilms of the current testing protocol were subjected to CDA at concentrations greater than 100× stronger (~0.05 ppm, 310 nM) than suggested in the literature, no observed dispersion of biofilm was observed. This test indicates that the recognized effect of CDA as reported in the literature, and perhaps other known dispersants, is determined, in part, by the robustness of the biofilm being treated.

Example 1 (CDA Dose Response)

A dose-response study was performed on mature biofilms with CDA at various concentrations in a solution of 5% DMSO. CDA was tested at concentrations of 50 ppm, 100 ppm, 200 ppm, 300 ppm, and 400 ppm. The mature biofilms were exposed to CDA over a period of 24 hours. to measure the efficacy of the fatty acid.

Figure 3C:
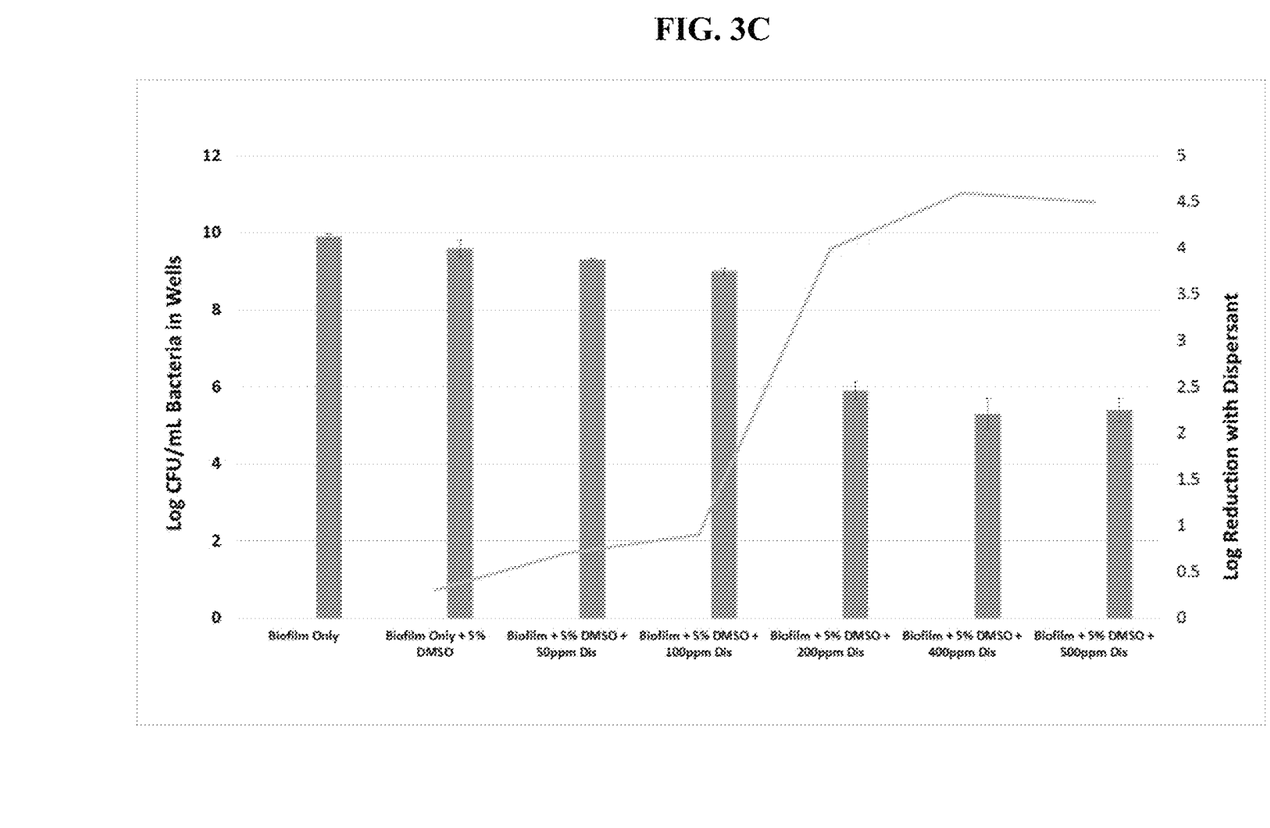
FIG. 3C provides dose-response data for CDA after 24 hr. treatment of S. aureus (ATCC 25923) biofilms grown for 48 hrs.
Figure 4:
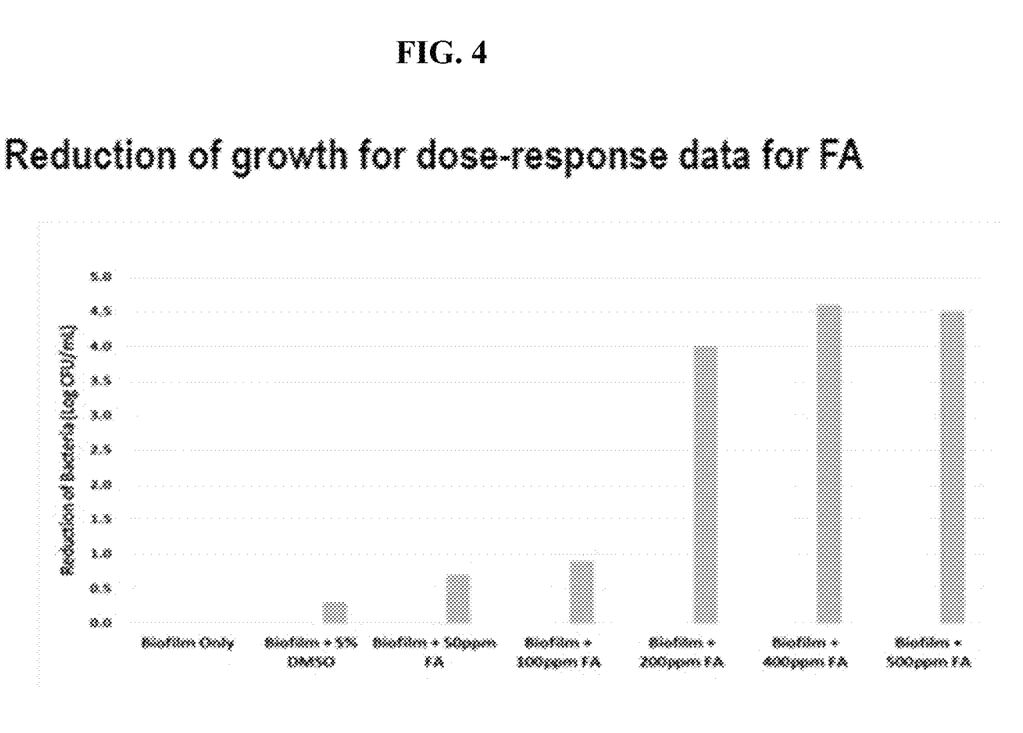
FIG. 4 provides dose-response data in bar graph form for CDA after 24 hr. treatment of S. aureus (ATCC 25923) biofilms grown for 48 hrs.

The bars in FIG. 3C show the Log CFU count/ml of the bacteria after 24 hours. exposure to CDA, along with a control of a) biofilm only, and b) biofilm+5% DMSO, in order to account for any effect of the DMSO. The line in FIG. 3C represents the log reduction in CFU count (Log CFU count for the Biofilm control−Log CFU count CDA sample=Log reduction). FIG. 4 also shows the same log reduction values, but in bar graph form.

Surprisingly, the data shows that CDA was not only acting as a dispersant, but in fact, had a bactericidal effect on the biofilm. Even more unexpected, there was a significant spike in the bactericidal effect of CDA at concentrations greater than 100 ppm, and a greater than 4-fold log reduction in CFU in concentrations at 200 ppm or greater.

Example 2 (CDA+Antibiotics)

Based upon the results from Example 1, the activity of CDA at a concentration of 400 ppm was measured in combination with gentamicin, cefazolin, and vancomycin on K-wires having mature biofilms grown for 48 hours.

Figure 5A:
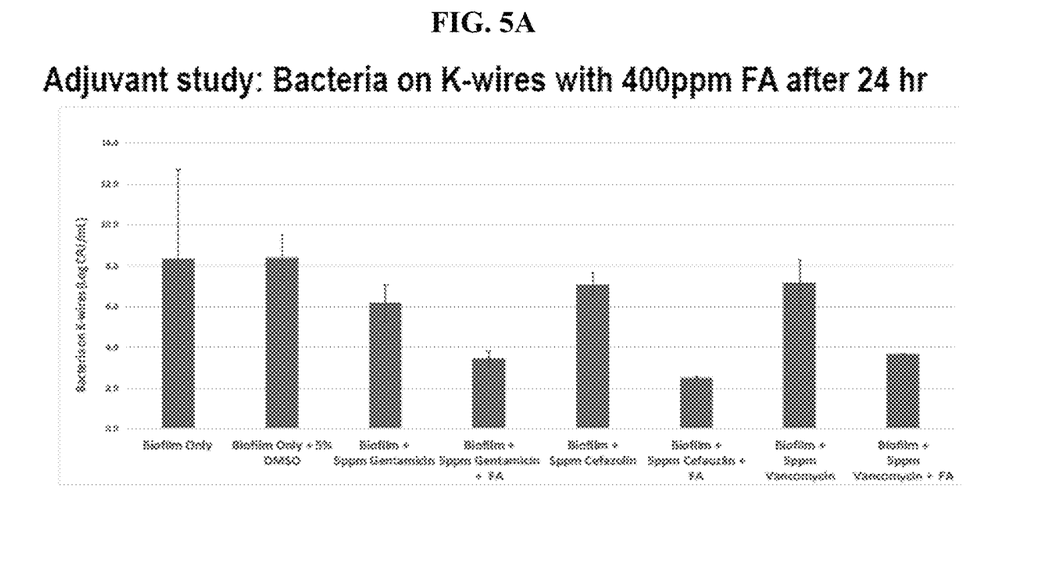
FIGS. 5A-5B and FIGS. 6A-6B depict the results of a study involving the measurement of the activity of CDA at a concentration of 400 ppm in combination with gentamicin, cefazolin, and vancomycin on K-wires having mature biofilms grown for 48 hours.
Figure 5B:
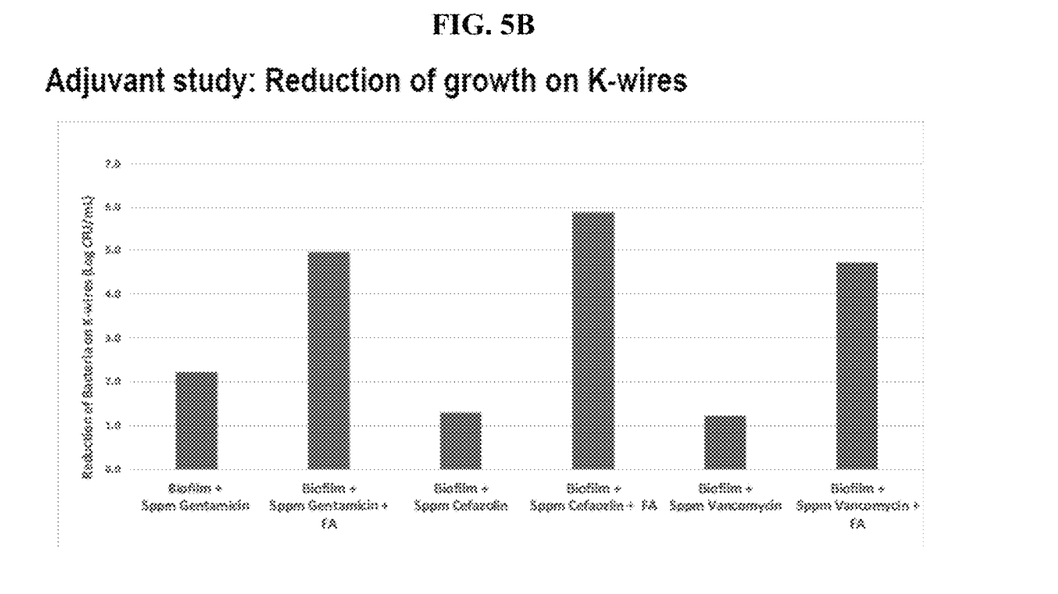
Figure 6A:
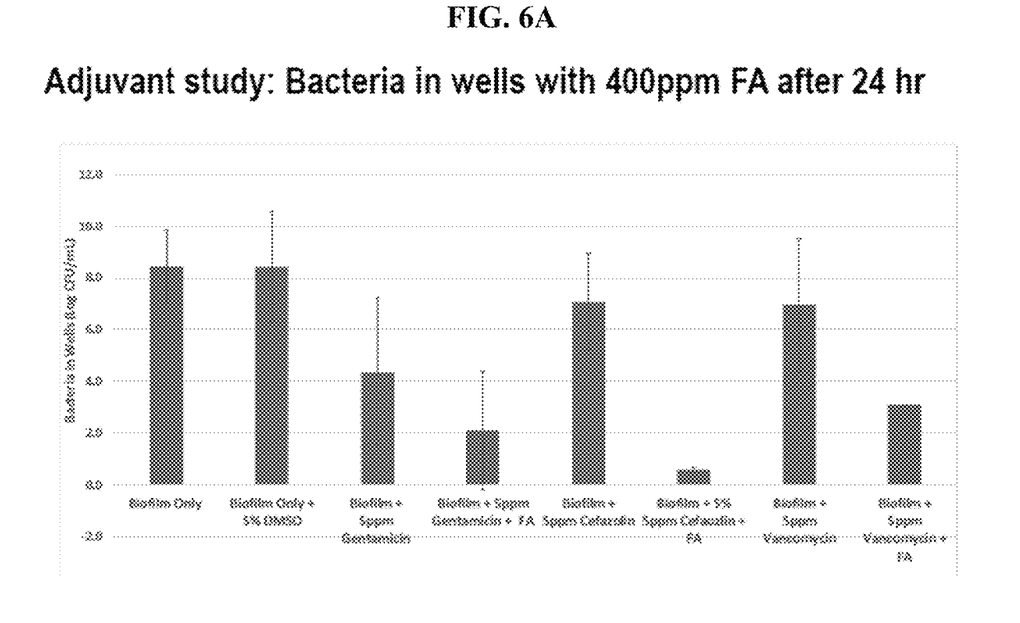
Figure 6B:
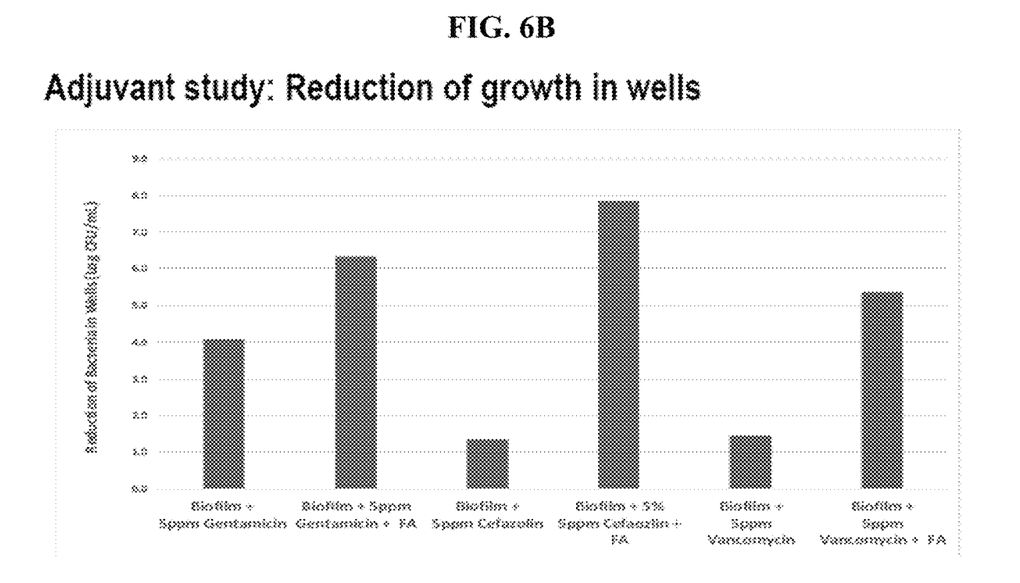

Following growth, biofilms were washed and treated with the fatty acid and/or antimicrobials to determine dose-response and adjuvant effects. After this time, the wells of the samples were diluted and plated to determine dispersion levels compared to controls. The K-wires were washed, sonicated to remove any residual cells, and the samples were plated to determine CFU/mL. As can be seen in FIGS. 5A-B, treatment of the K-wires with the adjuvant produced a 4.9, 5.9, and 4.7 log reduction of bacteria on the medical device in combination with gentamicin, cefazolin, and vancomycin, respectively. In addition, as shown in FIGS. 6A-B, the fatty acid adjuvant resulted in a significant 6.3, 7.8, and 5.3 log reduction of bacteria in the wells for gentamicin, cefazolin, and vancomycin, respectively.

Example 3 (1 Hour CDA/Cefazolin)

The goal of this study was to determine whether the combination of CDA and Cefazolin can act quickly on a debrided contaminated wound site with an adjuvant killing effect of CDA and a therapeutic drug concentration. The biofilm was grown at 30° C. and the same 0.3% (w/v) media used in previous studies was used in this study. The biofilm was grown for 48 hours, then underwent a mechanical "debridement" process. This debridement was done to simulate the debridement of an infected wound site. After the physical removal of visual biofilm, the K-wires were exposed to 400 ppm CDA, 10 ppm cefazolin, or a combination of both, for one hour (in contrast to the previous studies where exposure was for 24 hrs). Separately, a test was conducted on an untreated biofilm (i.e., not debrided) using a higher concentration of CDA, approximately 800 ppm. This concentration of CDA was determined to be the MIC value for ATC 25923 planktonic cells as noted above in the previous example.

The contents of the wells and bacteria on the K-wires were diluted and plated to determine CFU/mL. Briefly, the K-wires were secured to tube caps and placed in tubes incubated with an initial inoculum concentration ($10^5$ CFU/mL) and grown for 24-48 hours. Media was changed roughly every 8 hours. After growth, the biofilms were exposed to a combination of CDA and cefazolin for 60 minutes.

After exposure time was completed, both the well samples and the debrided K-wires were treated, and the remaining bacteria cells were plated and counted. For the media in the wells, samples were centrifuged for 10 minutes at 3000 rpm and the supernatant was removed. The cells were resuspended in 10 mL 1×PBS buffer. This washing step was repeated for a second time and the cells resuspended again in a final volume of 1.5 mL neutralizing buffer, diluted and plated on Tryptic Soy Agar with Lectin (TSA-L) agar plates. For the K-wires, the caps securing the K-wires in the tubes were removed and transferred to tubes with 10 mL 1×PBS and the tubes were inverted. The cap with the K-wires were transferred again to another tube with PBS and the step was repeated. After washing the K-wires 2×, they were transferred to tubes with neutralizing buffer and vortexed followed by ultra-sonication for 10 minutes. The cells were then diluted and plated on TAS-L agar plates.

Below is the procedure outlined in greater detail.

Procedure:

Prepare an overnight bacterial inoculum of S. aureus at a concentration of $10^9$ CFU/mL in 20 mL in commercial TSB by incubating at 37° C. shaker at 250 rpm.

Take an OD600 reading of a diluted stock of overnight culture to determine stock concentration with the absorbance method.

Adjust the concentration of bacteria to $10^5$ CFU/mL using 0.3% (w/v) TSB making sure to forcibly aspirate up and down to break up clumps of colonies with a serological pipette from the stock concentration.

Plate the following dilutions in triplicates on TSA-L plates to determine the initial stock concentration of cells: $10^2$ CFU/mL.

Add 7 mL of inoculum into each 15 ml tube containing K-wire using a serological pipette, making sure to again forcibly aspirate up and down prior to addition.

Place the tubes on the revolver at 30° C.

After 8 hours, unscrew the caps and transfer the caps with sutures to a new tube with 7 mL of 0.3% TSB and incubate in the shaker-incubator for an additional 44 hours to grow the biofilm at 40 RPM growing.

During this time, change the media 2× per day by unscrewing the cap and transferring to a new tube with 7 mL TSB. After 48 hours of growth, proceed with debridement of the biofilm and exposure.

Exposure to CDA and/or Cefazolin:

Transfer the K-wires in new tubes containing 10 mL of 1×PBS, invert it two times and repeat the same step with one more PBS wash by inverting 2 times for a total of 2 washes.

After the Wash:

Transfer caps with debrided biofilm to a new tube containing 10 mL of 0.1% TSB with DMSO only.

Transfer caps with debrided biofilm to a new tube containing 10 mL of 0.1% TSB+400 ppm concentration of CDA+5% DMSO.

Transfer caps with debrided biofilm to a new tube containing 10 mL of 0.1% TSB+10 ppm concentration of cefazolin.

Transfer caps with debrided biofilm to a new tube containing 10 mL of 0.1% TSB+10 ppm concentration of cefazolin+400 ppm CDA+5% DMSO.

Transfer caps with FULL biofilm to a new tube containing 10 mL of 0.1% TSB+10 ppm concentration of cefazolin+800 ppm CDA+5% DMSO.

Incubate all caps and tubes at 21° C. for 60 minutes on the revolver (horizontally) set at 40 RPM. The lower media concentration and room temperature were chosen to lower planktonic cell proliferation in the wells of the sample and so to better decouple the effect of the dispersant.

Cover the samples with aluminum foil as CDA is light sensitive. If on revolver, foil the entire shaker incubator.

After the exposure time, transfer the caps with wires to a new tube with 1×PBS and wash 2× to remove any CDA.

For K-wires, transfer to a tube with neutralizing buffer, vortex for 10 seconds. Sonicate for 15 minutes on ice. Use the rubber policeman to remove all biofilm from the surface of the K-wire. Rinse each K-wire with 1 mL of neutralizing buffer, then the rubber policeman with another 1 mL of neutralizing buffer. Dilute the bacteria and plate the cells to determine CFU/mL.

For wells, centrifuge the tubes at 3000 rpm for 10 minutes. Remove the supernatant and resuspend the cells in 10 mL 1×PBS. Repeat centrifugation and resuspension of cells in 10 mL 1×PBS and then finally resuspend the cells in 1.5 mL neutralizing buffer. Then dilute the bacteria and plate the cells to determine CFU/mL. The results are shown below in Tables 1 and 2.

TABLE 1

| | K-Wire Testing | | | | |
|---|---|---|---|---|---|
| | Debrided Biofilm | 400 ppm CDA | 10 ppm Cef | 10 ppm Cef + 400 ppm CDA | Full Biofilm + 800 ppm CDA + 10 ppm Cef |
| Avg. Log CFU | 9.4 | 7.8 | 8.5 | 7.5 | 5.5 |
| Reduction | N/A | 1.6 | 0.9 | 1.9 | 3.9 |

TABLE 2

| | Well Testing | | | | |
|---|---|---|---|---|---|
| | Debrided Biofilm | 400 ppm CDA | 10 ppm Cef | 10 ppm Cef + 400 ppm CDA | Full Biofilm + 800 ppm CDA + 10 ppm Cef |
| Avg. Log CFU | 6.2 | 5.6 | 5.4 | 5.8 | 1.5 |
| Reduction | N/A | 0.6 | 0.8 | 0.5 | 4.8 |

What is claimed:

1. A composition for treating bacterial biofilm-mediated infection comprising: a cis-monounsaturated fatty acid solubilized in a solvent and having a concentration in the range of about 100400 ppm to about 1000 ppm; and, an antibiotic drug in a concentration of about 5-15 ppm; wherein the composition provides a log reduction in the range of greater than 2.0 to greater than 6.5 as compared to the log reduction of a composition comprising the antibiotic drug in the absence of the cis-monosaturated fatty acid, wherein the cis-monosaturated fatty acid is a cis-2-alkenoic acid and wherein the antibiotic drug is an aminoglycoside, a cephalosporin, or a glycopeptide antibiotic, or a combination thereof.

2. The composition of claim 1, wherein the concentration of the cis-monosaturated fatty acid is in the range of about 200 ppm to about 500 ppm.

3. The composition of claim 1, wherein the concentration of the cis-monosaturated fatty acid is in the range of about 200 ppm to about 400 ppm.

4. The composition of claim 1, wherein the concentration of the cis-monosaturated fatty acid is in the range of about 400 ppm to about 800 ppm.

5. The composition of claim 1, wherein the concentration of the cis-monosaturated fatty acid is about 400 ppm.

6. The composition of claim 1, wherein the cis-2-alkenoic acid is cis-2-decenoic acid (CDA), cis-9-octadecanoic acid (oleic acid), or cis-11-methyl-2-dodecenoic acid, or a combination thereof.

7. The composition of claim 6, wherein the cis-2-alkenoic acid is CDA.

8. The composition of claim 6, wherein the composition comprises a combination of CDA and at least one of cis-9-octadecanoic acid (oleic acid), or cis-11-methyl-2-dodecenoic acid.

9. The composition of claim 1, wherein the solvent is dimethyl sulfoxide (DMSO) chloroform, dimethyl formamide (DMF), or ethanol, or a mixture thereof.

10. The composition of claim 9, wherein the solvent is DMSO.

11. The composition of claim 1, wherein the composition of the antibiotic drug is in the range of about 5 ppm to about 10 ppm.

12. The composition of claim 1, wherein the antibiotic drug is gentamicin, cefazolin, or vancomycin, or a combination thereof.

13. The composition of claim 1, wherein the biofilm is a mature biofilm having grown for about 48 hours.

14. The composition of claim 1, wherein the biofilm is attached to an outer surface of an implantable medical device.

15. The composition of claim 1, wherein the log reduction is at least 4.0 after the biofilm has been exposed to the composition for a time period in the range of 12-36 hours.

16. The composition of claim 15, wherein the log reduction is at least 4.5.

17. The composition of claim 15, wherein the composition has a log reduction in the range of at least about 4.0 to about 8.0.

18. The composition of claim 1, wherein the composition is encapsulated in a liposome or micelle.

19. A method of treating a biofilm-derived infection site comprising: identifying a site including a biofilm; and, applying a composition of claim 1 to the site, wherein the composition is configured to produce a bactericidal effect measured as a log reduction of colony forming units (CFU) of a bacteria of at least 1.0 when the composition is applied to a biofilm formed from the bacteria.

20. The method of claim 19, wherein the site is a chronic wound infection site.

21. The method of claim 19, wherein the site is a surgical site.

22. The method of claim 21, wherein the surgical site includes an implantable medical device.

23. The method of claim 22, wherein the step of applying includes applying the composition to an outer surface of the medical device.

24. The method of claim 19, wherein the step of applying includes applying the composition to an absorbent material and contacting the absorbent material to the site.

25. The method of claim 19, further comprising the step of debriding at least a portion of the biofilm from the infection site.

26. The method of claim 19, wherein the step of applying can include more than one application of the composition to the site.

27. A method of inhibiting biofilm formation at a wound or surgical site comprising:
identifying a wound or surgical site susceptible to biofilm-derived infection; and,
applying a composition of claim 1 to the site, wherein the composition is configured to produce a bactericidal effect measured as a log reduction of colony forming units (CFU) of a bacteria of at least 1.0 when the composition is applied to a biofilm formed from the bacteria.

28. The method of claim 27, wherein the surgical site is a surgical site for receiving an implantable medical device, and wherein the method further comprises the step of implanting the medical device to the surgical site.

29. The method of claim 28, wherein the step of applying comprises applying the composition to an outer surface of the implantable medical device.

30. The method of claim 29, wherein the composition is applied to the outer surface of the implantable medical device before the device is implanted into the surgical site.

31. The method of claim 29, wherein the composition is applied to the outer surface of the implantable medical after the device is implanted into the surgical site.

* * * * *

UNITED STATES PATENT AND TRADEMARK OFFICE
CERTIFICATE OF CORRECTION

| | | |
|---|---|---|
| PATENT NO. | : 11,826,333 B2 | Page 1 of 1 |
| APPLICATION NO. | : 17/193196 | |
| DATED | : November 28, 2023 | |
| INVENTOR(S) | : Malavosklish Bikram-Liles et al. | |

It is certified that error appears in the above-identified patent and that said Letters Patent is hereby corrected as shown below:

In the Claims

Column 12, Line 43, Claim 1, delete "100400" and replace with --400--;

Column 12, Lines 48, 49, 54, 57, 60 and 63, Claim 1, delete "cis-monosaturated" and replace with --cis-monounsaturated--.

Signed and Sealed this
Twelfth Day of March, 2024

Katherine Kelly Vidal
*Director of the United States Patent and Trademark Office*